United States Patent [19]

Noiles

[11] Patent Number: 4,634,444
[45] Date of Patent: Jan. 6, 1987

[54] SEMI-CONSTRAINED ARTIFICIAL JOINT

[75] Inventor: Douglas G. Noiles, New Canaan, Conn.

[73] Assignee: Joint Medical Products Corporation, Stamford, Conn.

[21] Appl. No.: 578,437

[22] Filed: Feb. 9, 1984

[51] Int. Cl.⁴ .............................................. A61F 2/38
[52] U.S. Cl. ..................................................... 623/20
[58] Field of Search .................... 3/1, 1.9, 1.91, 1.911, 3/1.912, 1.913; 128/92 C; 623/16, 17, 18, 19, 20, 21, 22, 23

[56] References Cited

U.S. PATENT DOCUMENTS

| | | | |
|---|---|---|---|
| 3,816,853 | 6/1974 | Elson | 3/1 |
| 3,848,276 | 11/1974 | Martinez | 3/1 |
| 3,953,899 | 5/1976 | Charnley | 3/1.911 |
| 3,996,624 | 12/1976 | Noiles | 3/1.911 |
| 4,209,861 | 7/1980 | Walker et al. | 3/1.911 |
| 4,219,893 | 9/1980 | Noiles | 3/1.911 |
| 4,301,553 | 11/1981 | Noiles | 3/1.911 |

FOREIGN PATENT DOCUMENTS

| | | | |
|---|---|---|---|
| 2227090 | 12/1973 | Fed. Rep. of Germany | 3/1.911 |
| 2501128 | 7/1976 | Fed. Rep. of Germany | 623/20 |
| 2269324 | 1/1976 | France | 623/20 |
| 2478462 | 9/1981 | France | 623/20 |

Primary Examiner—Richard J. Apley
Assistant Examiner—David J. Isabella
Attorney, Agent, or Firm—Maurice M. Klee

[57] ABSTRACT

An artificial joint having stepped convex and concave bearing surfaces is provided. The stepped configuration prevents the bearing surfaces from sliding past one another along their axis of rotation and thus stabilizes the joint against lateral dislocations. In certain preferred embodiments, the stepped bearing surfaces faces are employed in an artificial knee joint and the joint is further stabilized against dislocations corresponding to the femur moving anteriorly with respect to the tibia.

16 Claims, 12 Drawing Figures

SEMI-CONSTRAINED ARTIFICIAL JOINT

BACKGROUND OF THE INVENTION

1. Field of the Invention

This invention relates to semi-constrained artificial joints and in particular to semi-constrained artificial knee joints.

2. Description of the Prior Art

In U.S. Pat. Nos. 4,219,893 and 4,301,553, issued to me on Sept. 2, 1980 and Nov. 24, 1981, respectively, there is described a prosthetic joint, e.g., a prosthetic knee joint, which permits rotation in two planes. The joint includes a femur component which carries convex bearing surfaces, a tibia sleeve component which, in the preferred embodiments, carries a flat bearing surface lying in a plane essentially orthogonal to the axis of the tibia, and an intermediate component having top and bottom bearing surfaces which mate with the bearing surfaces on the femur and tibia sleeve components, respectively.

Flexion of this knee joint occurs by the bearing surfaces on the femur component and the top of the intermediate component moving with respect to one another. Normal rotation of the tibia about its longitudinal axis as the knee moves from a fully extended to a flexed position occurs by the bearing surfaces on the tibia sleeve component and the bottom of the intermediate component moving with respect to one another. Additional rotation of the tibia in response to torque loads on the foot is also accommodated in this manner to the extent that the ligaments, tendons, etc., surrounding the knee joint will permit.

In the most preferred embodiments of the prosthetic knee joint described in the above patents, the femur component and the intermediate component are hinged together by a rigid coupling of the type shown in U.S. Pat. No. 3,996,624, issued to me on Dec. 14, 1976. In practice, prostheses constructed in this manner have been found to provide highly stable reconstructions for patients whose joints and surrounding tissues have undergone severe deterioration prior to implantation of the prosthesis.

For certain patients, artificial joints are rigid as those which result from using the coupling of U.S. Pat. No. 3,996,624 are not required because the patient's own tissues, at least to some extent, are able to hold the components of the artificial joint in place. In the art, such artificial joints which rely on the patient's anatomy for a certain amount of stability and which have components which are not rigidly connected to one another, are referred to as "semi-constrained".

U.S. Pat. Nos. 4,219,893 and 4,301,553 referred to above include a disclosure of two semi-constrained embodiments employing a femur component, an intermediate component and a tibia sleeve component. The present invention is directed to improving these semi-constrained embodiments.

In particular, it is an object of the present invention to provide an artificial joint of the semi-constrained type which provides for both flexion of the joint and rotation of the tibia about its longitudinal axis, which employs bearing surfaces of large area for flexion, and in which the bearing surfaces are partially stabilized against dislocations in the direction of their axis of rotation, but are not constrained from moving apart in a direction orthogonal to the axis of rotation.

It is a further object of the invention to provide an artificial joint of the above type in which the bearing surfaces are also partially stabilized against anterior dislocations of the femur with respect to the tibia. It is an additional object of the invention to provide an artificial joint stabilized in both of the foregoing ways which allows the cylindrical bearing surfaces to come apart in a manner which permits the patient's lower leg to move laterally with respect to his upper leg, i.e., to articulate in a manner which permits movement of the tibia with respect to the femur in a plane passing through the longitudinal axis of the tibia and through the axis of rotation of the bearing surfaces. Such movement is described medically as in a varus or valgus direction. Because the joint of the present invention is free to move in this manner, patients in which the joint is to be implanted must have collateral ligaments which are sufficiently functional to prevent excessive varus or valgus movement.

SUMMARY OF THE INVENTION

To achieve the above and other objects, the invention, in accordance with one of its aspects, provides an artificial joint having mating convex and concave bearing surfaces which extend essentially across the whole width of the prosthesis. So that the bearing surfaces can move apart in a direction orthogonal to their axis of rotation, the concave surface encompasses less than one-half of the perimeter of the convex surface.

Each of the convex and concave bearing surfaces is divided into three parts which mate with the corresponding three parts on the other bearing surface, the outer two parts having a radius of curvature different from that of the middle part, e.g., a greater radius of curvature. The outer parts of each bearing surface are connected to the inner part by walls so that, in toto, each bearing surface has a stepped configuration. This stepped configuration prevents the convex and concave bearing surfaces from sliding over one another along their axis of rotation and thus stabilizes the joint against dislocations along this axis.

In certain preferred embodiments of the invention, the bearing surfaces are further stabilized against selected dislocations in a direction orthogonal to their axis of rotation, e.g., for knee joints, dislocations corresponding to the femur moving anteriorly with respect to the tibia. This is accomplished by including a stop for the convex bearing surface as part of the joint. Preferably, the stop comprises an extension of the concave bearing surface, e.g., for knee joints, an extension of the anterior edge of the concave bearing surface. Most preferably, only a part of the concave surface is extended, e.g., the part corresponding to the middle of the three parts making up that surface.

For a stop of the above type, it is further preferable to contour the stop so that it does not interfere with lateral articulation of the bearing surfaces with respect to each other, e.g., for a knee joint, so that it does not interfere with varus or valgus motion of the patient's lower leg with respect to his upper leg. In this way, the stop does not have to be made mechanically strong enough to resist the large forces involved in preventing excessive varus-valgus motions. This is preferable because it means that the stop can have relatively small dimensions and can be made of relatively weak materials, such as plastics. A stop of this type, however, does require that the patient's ligaments be sufficiently intact to themselves prevent excessive varus-valgus motions.

Alternatively, the stop can have a design which is mechanically adequate to resist varus-valgus deflection tendencies, in which case, the patient's ligaments need not be as structurally sound.

The accompanying drawings, which are incorporated in and constitute part of the specification, illustrate the preferred embodiments of the invention, and together with the description, serve to explain the principles of the invention. It is to be understood, of course, that both the drawings and the description are explanatory only and are not restrictive of the invention. In particular, it is to be understood that although, for ease of discussion, the description which appears below is in terms of an artificial knee joint, the invention is equally applicable to other types of artificial joints, such as, artificial elbow joints and the like.

DESCRIPTION OF THE PREFERRED EMBODIMENTS

Figure 1:
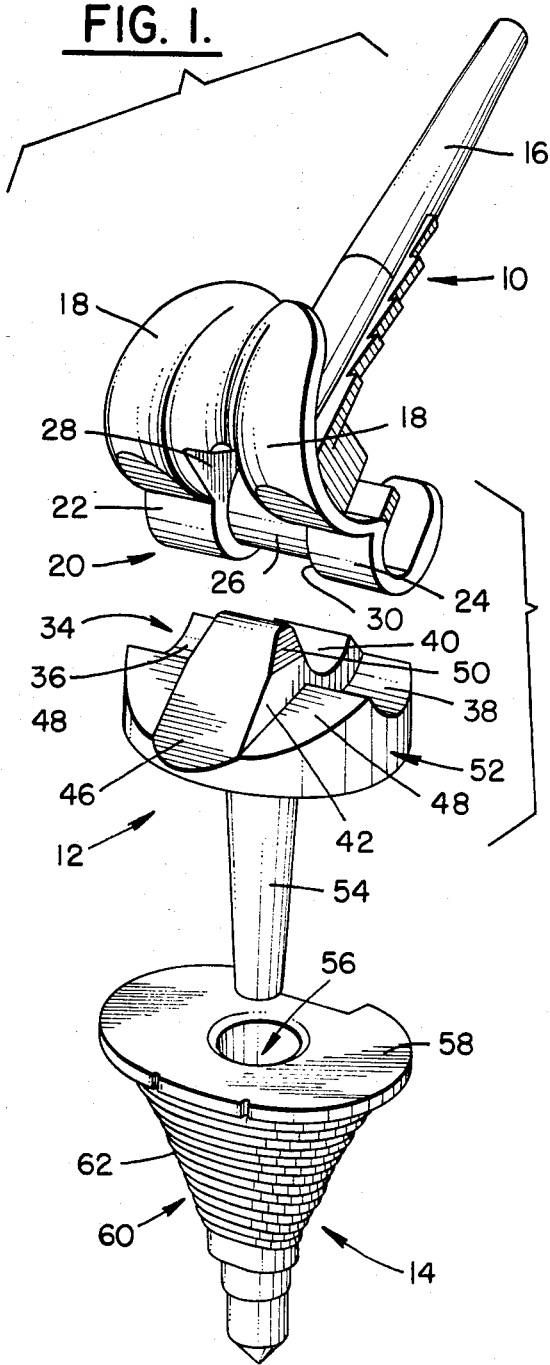
FIG. 1 is a perspective, exploded view of an artificial knee joint constructed in accordance with the present invention.
Figure 2:
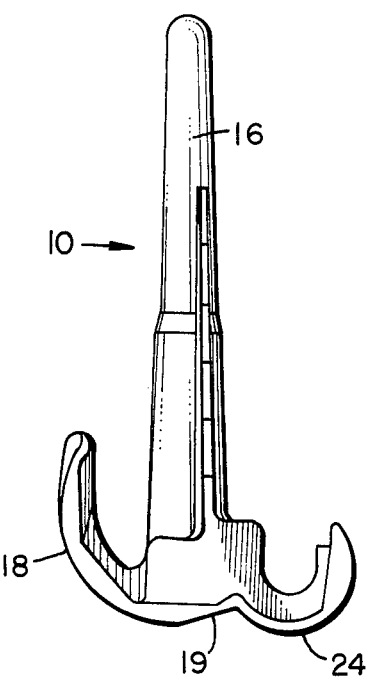
FIGS. 2 and 3 are side and bottom views, respectively, of the femur component of the joint of FIG. 1.
Figure 3:
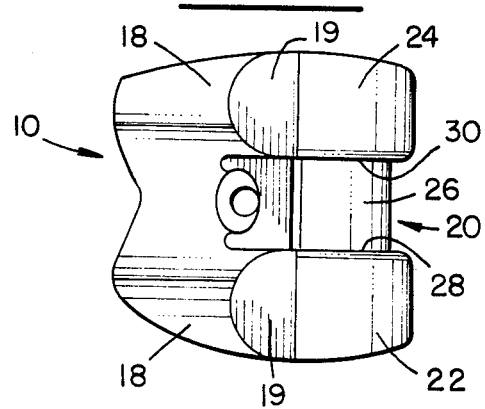
Figure 4:
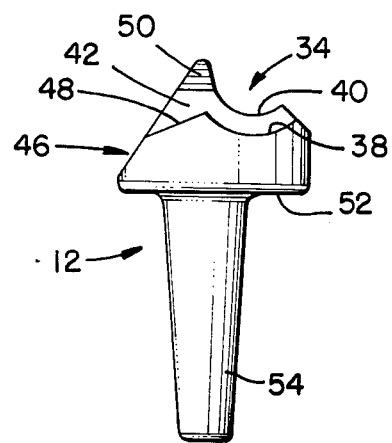
FIGS. 4 and 5 are side and top views, respectively, of the intermediate component of the joint of FIG. 1.
Figure 5:
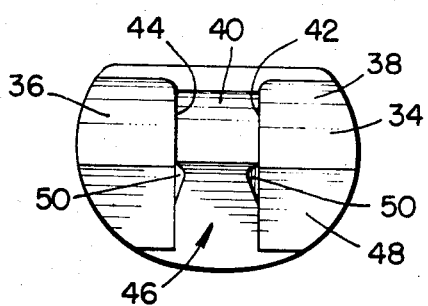

Referring now to the figures, there is shown in FIG. 1 an exploded view of an artificial knee joint constructed in accordance with the present invention. The joint includes a femur component 10, an intermediate component 12 and a tibia sleeve component 14.

Femur component 10 and intermediate component 12 respectively carry mating bearing surfaces 20 and 34, each having a stepped configuration. As shown in the figures, these bearing surfaces extend across the full width of the prosthesis so as to provide a large, wear-resistant bearing for flexion motions of the joint. Preferably, bearing surfaces 20 and 34 are surfaces of revolution, i.e., cylindrical in shape, although other bearing contours can be used in the practice of the invention. So that the bearing surfaces can come apart in a direction orthogonal to their axis of rotation, concave bearing surface 34 encompasses less than one-half of convex bearing surface 20.

Convex bearing surface 20 is composed of three parts: two outer parts 22 and 24 having a first radius of curvature, and middle part 26 having a different radius of curvature, specifically, as shown in the figures, a smaller radius of curvature. Concave bearing surface 34 has a corresponding set of three parts, i.e., outer parts 36 and 38 which have a larger radius of curvature and which mate with outer parts 22 and 24, respectively, and middle part 40 which has a smaller radius of curvature and which mates with middle part 26.

Outer parts 22 and 24 of convex bearing surface 20 are connected to middle part 26 by walls 28 and 30, respectively. Similarly, outer parts 36 and 38 of concave bearing surface 34 are connected to middle part 40 of that bearing surface by walls 44 and 42, respectively. The presence of these walls stabilizes the assembled joint against dislocations along the axis of rotation of bearing surfaces 20 and 34. Specifically, the engagement of wall 30 with wall 42, or, wall 28 with wall 44, limits the lateral motion of surfaces 20 and 34 with respect to one another. Significantly, this stabilization is achieved without sacrificing the overall width of bearing surfaces 20 and 34, as would occur with other modes of lateral stabilization known in the art, such as, through the use of a post or the like between two laterally separated bearing surfaces.

As shown in the figures, the outer parts of the bearing surfaces have common radii of curvature, and those radii of curvature are larger than the radii of curvature of the inner parts. It is to be understood that the parts making up the bearing surfaces can have radii of curvature other than those shown, provided that the radii are such that their differences produce walls 28,30 and 42,44 of sufficient height to restrain the bearing surfaces against lateral dislocations. For example, the inner parts of the bearing surfaces can be given larger radii of curvature than the outer parts. Similarly, the two outer parts need not have the same radius of curvature, but each outer part can have its own radius of curvature, if desired.

Figure 8:
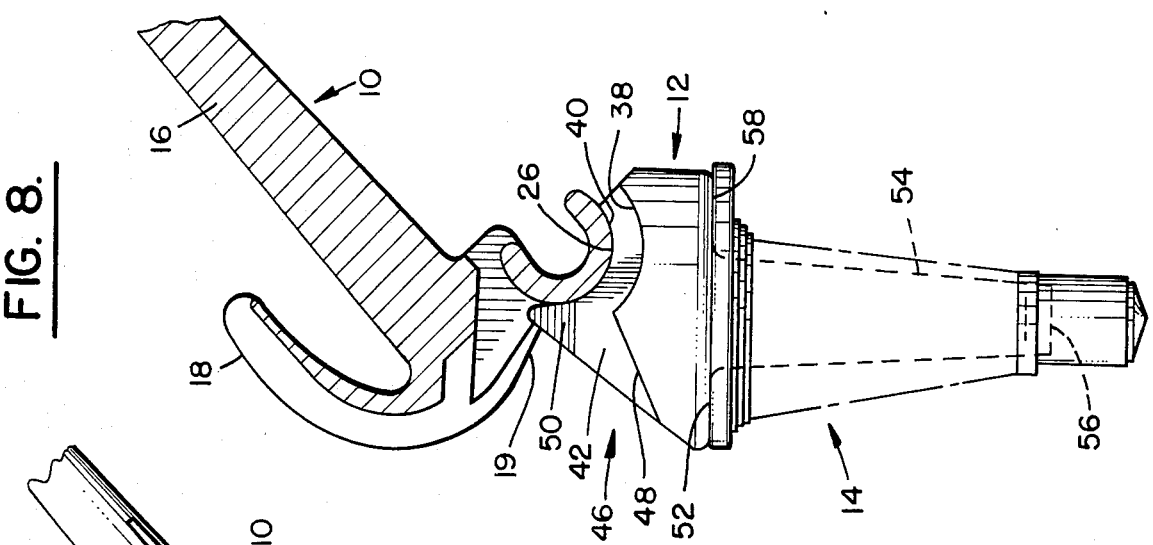
FIG. 8 is a cross-sectional view along lines 8—8 in FIG. 6.
Figure 7:
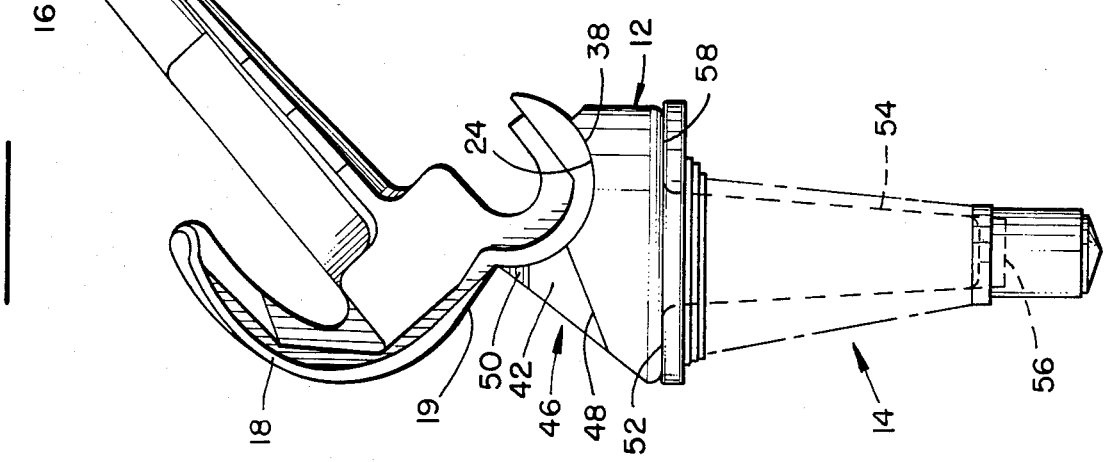
FIGS. 6 and 7 are front and side views, respectively, of the joint of FIG. 1 at a flexion angle of approximately 45°.
Figure 9:
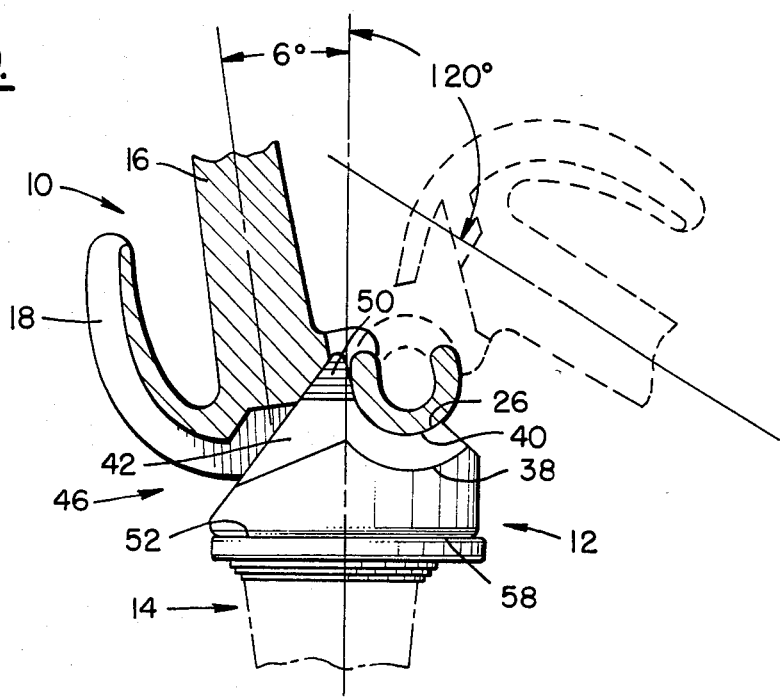
FIG. 9 is a cross-sectional view along the midline of the prosthesis showing the range of motion of the femur component of the joint with respect to the intermediate component.

In addition to being stabilized against lateral dislocations, the joint of the present invention is also stabilized against anterior dislocations of the femur with respect to the tibia, i.e., movement of femur component 10 towards the left in FIGS. 7-9 relative to intermediate component 12. This is accomplished by means of stop 46.

As can best be seen in FIG. 8, the posterior portion of stop 46 comprises an anteriorly sloping continuation of inner part 40 of concave bearing surface 34. This continuation restrains part 26 of convex bearing surface 20 from moving anteriorly and thus provides the desired anterior stabilization of femur component 10 relative to intermediate component 12.

Rather than sloping anteriorly, the continuation of inner part 40 of concave bearing surface 34 can be vertical, or can even slope posteriorly, if desired. An anterior slope is preferred, however, because it ensures that femur component 10 will not bind against stop 46 during hyperextension of the knee. Such binding could break off a portion of stop 46, especially when intermediate component 12 is composed of a plastic material, as is preferred.

Along these same lines, stop 46 is not used to limit the hyperextension range of the joint (see FIG. 9), but rather the contacting of flat portions 19 of patellar surfaces 18 (see, for example, FIG. 7) with sloping surfaces 48 on intermediate component 12 are used for this purpose. Furthermore, between walls 28 and 30, a cavity is formed in femur component 10 having contours which will not bind against stop 46 at any point during flexion of the joint, e.g., as shown in FIG. 9, from a fully bent position of 120° to a hyperextended positn of 6°.

Although the interface between femur component 10 and intermediate component 12 is designed to constrain the joint against lateral and anterior dislocations, it is specifically designed not to constrain the joint with regard to varus or valgus rotations of the tibia with respect to the femur. As discussed above, this non-constraint means that the collateral ligaments of the patient must function to stabilize the joint with respect to varus-valgus articulation.

Figure 6:
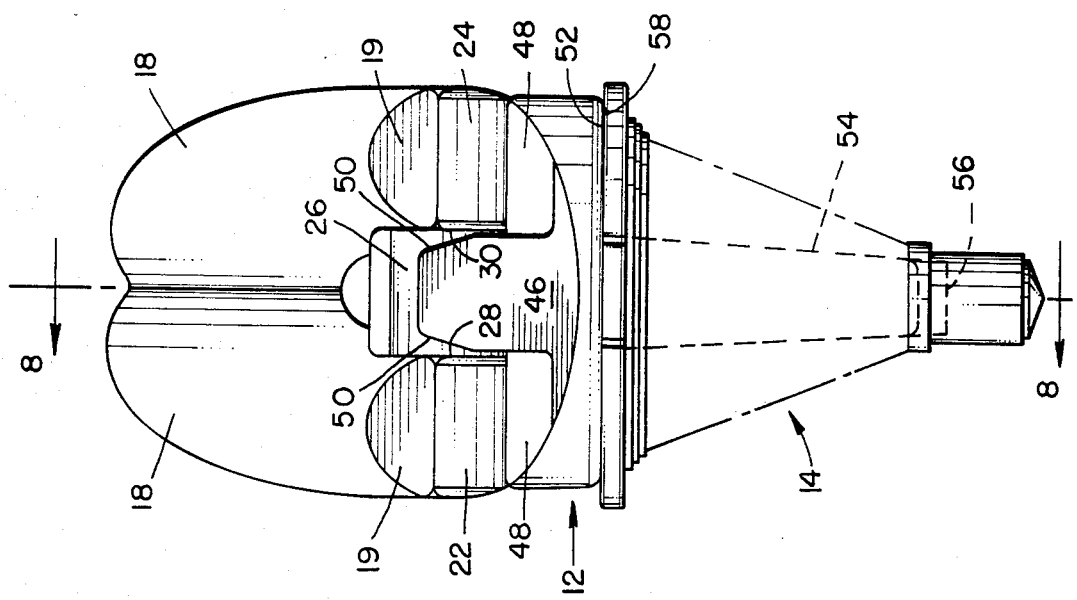

These varus or valgus articulations are effectuated in the joint of the present invention by bearing surface 34 pivoting about either the left or the right hand outer edge of bearing surface 20 so as to bring bearing surfaces 20 and 34 out of engagement. to allow this motion to occur without binding of stop 46 against walls 28 or 30, the upper portion of the stop is chamfered at 50. As can best be seen in FIG. 6, this chamfering provides adequate clearance between stop 46 and walls 28 and 30 during lateral rotations of the patient's lower leg with respect to his upper leg.

Figure 11:
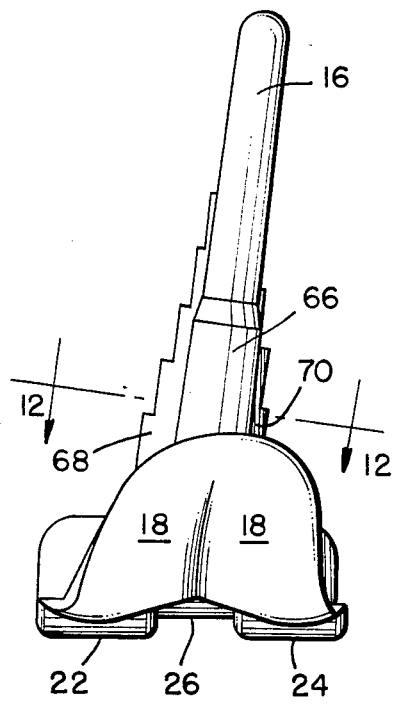
FIG. 11 is a front view of the femur component of the joint of FIG. 1.
Figure 12:
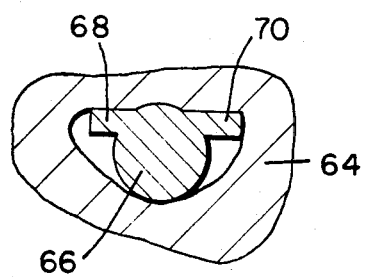
FIG. 12 is a cross-sectional view along lines 12—12 in FIG. 11 showing how the shank of the joint's femur component fits within the patient's femur.

In addition to carrying convex bearing surface 20 and patellar surfaces 18, femur component 10 also includes fixation shank 16 which is adapted to be implanted in the patient's femur using standard surgical techniques. As shown most clearly in FIGS. 11-12, this shank includes an elongated cone portion 66 having flanges 68 and 70 at the large end of the cone. The flanges are oppositely opposed, tangent to the cone, and coplanar. As illustrated in FIG. 12, this configuration results in an especially close fit between the shank of femur component 10 and the contour of the hard bone 64 making up the outer wall of a typical patient's femur.

Figure 10:
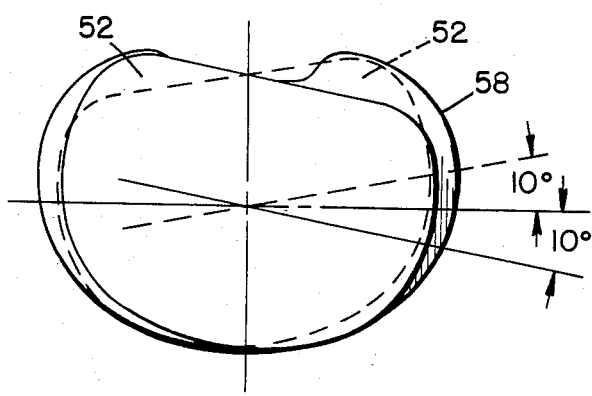
FIG. 10 illustrates the magnitude of the relative movement between the intermediate and tibia sleeve components which occurs in the joint of FIG. 1 as the tibia and femur move from a position of full extension to a position of flexion.

Similarly, in addition to concave bearing surface 34, stop 46, and sloping surfaces 48, intermediate component 12 also includes depending rod 54 and bearing surface 52 which forms the bottom of the component. In the assembled joint, bearing surface 52 mates with bearing surface 58, i.e., the top surface of tibia sleeve 14, and depending rod 54 is received in aperture 56 formed in the body of the tibia sleeve. As fully described in the above-referenced U.S. Pat. Nos. 4,219,893 and 4,301,553, the pertinent portions of which are incorporated herein by reference, this arrangement of these components allows tibia sleeve 14 to rotate with respect to intermediate component 12 as the femur and tibia move from a position of full extension to a position of flexion. As illustrated in FIG. 10, this rotation of the tibia about its longitudinal axis during flexion is normally on the order of about 10°.

Tibia sleeve component 14 is designed to be implanted in the upper portion of the tibia. Various approaches can be employed for this implantation. One such approach is that described in U.S. patent application Ser. No. 578,351, entitled "Apparatus for Affixing a Prosthesis to Bone," which is assigned to the same assignee as this application and is being filed simultaneously herewith. Briefly, this technique involves providing tibia sleeve 14 with an outer surface 60 which has been contoured to mate with a portion of the inner surface of the hard bone at the upper end of the tibia. In addition to being anatomically contoured, the surface is also provided with a texture 62 designed to increase its coefficient of friction with the hard bone. A further discussion of the technique can be found in the above-referenced patent application, the pertinent portions of which are incorporated herein by reference.

Femur component 10, intermediate component 12 and tibia sleeve 14 can be made out of a variety of biologically compatible, surgically implantable materials. For example, a cobalt-chromium-molybdenum alloy, such as that described in ASTM F75, can be used for femur component 10, a titanium-aluminum-vanadium alloy, such as that described in ASTM F136 can be used for tibia sleeve 14, and ultra-high molecular weight polyethylene (UHMWPE) can be used for intermediate component 12. Other types and combinations of materials appropriate for use in the artificial joint of the present invention will be evident to persons skilled in the art.

Although specific embodiments of the invention have been described and illustrated, it is to be understood that modifications can be made without departing from the invention's spirit and scope. For example, the stepped bearing surfaces described herein can be used to provide lateral stability to artificial joints having a variety of configurations different from the configuration illustrated herein. Similarly, a variety of stop means other than that illustrated can be used to stabilize the joint against dislocations of the type wherein the femur moves anteriorly with respect to the tibia.

What is claimed is:

1. An artificial joint which can be articulated between an extended and a flexed position about an axis of rotation, comprising:

a first component having a convex bearing surface which includes two outer parts and an inner part, the inner part having a radius of curvature different from the radius of curvature of each of the outer parts and being connected to each of those parts by a wall, said connecting walls being parallel to one another; and a second component having a concave bearing surface engageable with the convex bearing surface of the first component, said concave bearing surface including two outer parts and an inner part which respectively congruently mate with the outer and inner parts of the convex bearing surface of the first component, the inner part of the concave bearing surface being connected to each of the outer parts by a wall, said connecting walls being parallel to one another, and said connecting walls between the parts of the convex bearing surface being engageable with said connecting walls between the parts of the concave bearing surface when those bearing surfaces are engaged with each other so as to constrain the first and second components from moving relative to one another along the axis of rotation of the joint, the inner part of the convex bearing surface being able to remain in contact with the inner part of the concave bearing surface and the outer parts of the convex bearing surface being able to remain in contact with the outer parts of the concave bearing surface as the joint is articulated between its extended and flexed positions and the congruent mating of the parts of the conves bearing surface with the parts of the concave bearing surface constraining those surfaces from rotating relative to each other about an axis perpendicular to the axis of rotation of the joint.

2. The artificial joint of claim 1 wherein the convex and concave bearing surfaces extend across essentially the full width of the joint.

3. The artificial joint of claim 1 wherein the concave bearing surface encompasses less than one-half of the perimeter of the convex bearing surface.

4. The artificial joint of claim 1 wherein the convex and concave bearing surfaces are surfaces of revolution.

5. The artificial joint of claim 1 wherein the two outer parts of the convex bearing surface have the same radius of curvature.

6. The artificial joint of claim 5 wherein the radius of curvature of the two outer parts of the convex bearing surface is greater than the raduis of curvature of the inner part of that surface.

7. The artificial joint of claim 1 wherein the convex and concave bearing surfaces are surfaces of revolution which extend across essentially the full width of the joint, the concave surface encompasses less than one-half of the perimeter of the convex surface, the two outer parts of the convex surface have the same radius of curvature, and that radius of curvature is greater than the radius of curvature of the inner part of that surface.

8. The artificial joint of claim 1 further including means to partially constrain the convex and concave bearing surfaces from being dislocated in a certain direction orthogonal to the axis of rotation of the joint.

9. The artificial joint of claim 8 wherein the joint is an artificial knee joint and the certain direction corresponds to the femur moving anteriorly with respect to the tibia.

10. The artificial joint of claim 8 wherein the means comprises an extension of the concave bearing surface.

11. The artificial joint of claim 10 wherein the means comprises an extension of the inner part of the concave bearing surface.

12. The artificial joint of claim 11 wherein the joint is an artificial knee joint and the extension of the inner part of the concave bearing surface slopes anteriorly.

13. The artificial joint of claim 11 wherein the portion of the extension remote from the concave bearing surface is chamfered so as not to interfere with varus-valgus articulations of the convex and concave bearing surfaces with respect to each other.

14. The artificial join of claim 11 wherein the joint is an artificial knee joint and the portion of the extension remote from the concave bearing surface is chamfered so as not to interfere with articulations of the convex and concave bearing surfaces with respect to each other corresponding to varus or valgus motion of the tibia and femur.

15. The artificial joint of claim 11 wherein the joint is an artificial knee joint, the extension of the inner part of the concave bearing surface slopes anteriorly, and the portion of that extension remote from the concave bearing surface is chamfered so as not to interfere with articulations of the convex and concave bearing surfaces with respect to each other corresponding to varus or valgus motion of the tibia and femur.

16. The artificial joint of claim 15 wherein the convex and concave bearing surfaces are surfaces of revolution, the concave surface encompasses less than one-half of the perimeter of the convex surface, the two outer parts of the convex surface have the same radius of curvature, and that radius of curvature is greater than the radius of curvature of the inner part of that surface.

* * * * *